United States Patent [19]

Mercer

[11] 4,073,928
[45] Feb. 14, 1978

[54] THERAPEUTIC TREATMENT FOR VIRAL REGIONAL ILEITIS INFECTION

[76] Inventor: James B. Mercer, 13109 W. 95th St., Lenexa, Kans. 66215

[21] Appl. No.: 656,336

[22] Filed: Feb. 9, 1976

Related U.S. Application Data

[63] Continuation-in-part of Ser. No. 514,798, Oct. 15, 1974, Pat. No. 3,952,103.

[51] Int. Cl.² .......................................... A61K 31/415
[52] U.S. Cl. ................................................. 424/273 R
[58] Field of Search ........................................ 424/273

[56] References Cited
PUBLICATIONS

The Merck Manual, 12th ed., 1972, Merck & Co., Inc., N.J., pp. 717-719.

Primary Examiner—Jerome D. Goldberg
Attorney, Agent, or Firm—Fishburn, Gold & Litman

[57] ABSTRACT

The administration internally to humans of 1-($\beta$-hydroxethyl)-2-methyl-5-nitromidazole, (metronidazole) in a dosage range for adult humans of about 31 to 2,500 mgs per 24 hour period, is an effective therapeutic treatment for viral regional ileitis.

4 Claims, No Drawings

THERAPEUTIC TREATMENT FOR VIRAL REGIONAL ILEITIS INFECTION

This is a continuation-in-part of application Ser. No. 514,798 filed Oct. 15, 1974 entitled VIRAL INFECTION TREATMENT, now U.S. Pat. No. 3,952,103. Reference is also made to related U.S. Pat. Nos. 3,752,889 and 3,856,966.

The invention herein described relates to a method of treating viral regional ileitis in humans (Crohn's disease). The treatment also appears effective in the extension of life span which may result from the inhibition of such viral disease.

The objects of this invention are: to provide a method for systematically treating viral regional ileitis in humans; to provide such a treatment which is effective in combating viral infections in humans such as regional ileitis (Crohn's disease), to provide such a method which appears effective in the extension of life span which may result from the inhibition of this viral disease; to provide such a method that is suitable for intensive therapy as well as long-term maintenance and intermittent therapy; and to provide such a treatment which is easily administered and usually well tolerated by the recipient.

1-($\beta$-hydroxyethyl)-2-methyl-5-nitromidazole, (metronidazole) is a known alkylating agent of relatively low toxicity in mammals which is thought to interfere with nucleic acid biosynthesis. It appears that metronidazole can penetrate all tissues of the body quite readily and is effective, in the treatment of this viral infection. The agent apparently suppresses virus production while natural body defenses function to eliminate viral material from the system. Metronidazole is readily absorbable from the human intestinal tract and may be administered orally as well as by vaginal or rectal inserts, as indicated.

Clinical observations upon the administration of metronidazole have demonstrated marked patient improvement and in many cases, apparent complete remissions in statistically significant numbers of patients diagnosed as suffering from regional ileitis (Crohn's disease). The treatment often appeared effective in lengthening life and maintaining strength.

A typical intense treatment for an average size human adult patient comprises 500 mgs of the agent three to four times daily for a period of many months, then a reduction to 250 mgs three or four times daily for many additional weeks and thereafter further reduction or discontinuance, depending upon the tolerance of the patient and absence of symptoms. Doses for children and verterinary use are proportionally less according to body weight.

An ultimate effective long-time maintenance dose was found to be as low as 31 mgs per day. The most common effective maintenance dose has been determined to be about 250 mgs per day for a substantial percentage of patients, wit An ultimate effective long-time maintenance dose was found to be as low as 31 mgs per day. The most common effective maintenance dose has been determined to be about 250 mgs per day for a substantial percentage of patients, with 500 mgs per day being indicated and well tolerated for other patients, depending on age, size and physical condition. A reasonable maximum dosage for adult humans appears to be about 2,000 to 2,500 mgs per day. Renewal of treatment has been found to be effective upon a return of symptoms after treatment was discontinued.

Regarding side effects, some persons were found to experience nausea but it generally disappeared after a few weeks. In rare instances there was a slight soreness of the mouth or a white tongue indicating need for dosage reduction. Some dizziness and dryness of the mouth and vagina were occasionally noted and a few persons complained of a bad taste. Also, moderate leukopenia was occasionally observed, which normally returned to normal after dosage reduction, completion of a treatment regimen or as therapy continued.

Metronidazole is believed contraindicated in patients under treatment with desulfadram (Antabuse) and in uncompensated hypothyroid patients. Because metronidazole appears to cross the placental barrier and enter the fetal circulation rapidly and further since its effect on fetal development are not definitely known, it is also thought to be contrindicated during the first trimester of pregnancy, except when a history of prior existing viral infection may endanger that pregnancy.

The initial neurological signs of metronidazole overdose in humans appear to be increased pulse rate, difficulty in reading small print, difficulty in handling small objects and insomnia. Progressively, it is understood that tachycardia may occur, and a slightly unstable person, especially, may suffer marked swings in mood. Physical exercise apparently becomes increasingly fatiguing, and weight loss occurs to spite substantial food intake. When the medication is withdrawn, the adverse reaction usually clears in one week.

The metronidazole treatment described does not appear to damage the hematopoietic or the reticuloendothelial systems.

Over the past several years metronidazole has been tried with various effectiveness for the treatment of trichomonas vaginalis infections, alcholism, ameobic dysentery, ameobic liver abcess, leishmaniasis and giardia infestations, acute ulcerative gingivitis, long standing indolent ischemic ulcers found in peripheral vascular disease, scleroderma, schizophrenia and in diabetic retinopathy, but apparently its effectiveness in viral infections has not been heretofore known.

Metronidazole apparently interferes directly with the synthesis of DNA viruses, in a similar manner that occurs with cytosine arabinoside. Metronidazole also apparently interferes with protein synthesis, as uric acid levels increase during therapy and may in some instances manifest itself in acute gout.

It is to be understood that while certain practices of this invention have been described herein, it is not to be limited to the specific form described except insofar as such limitations are included in the following claims.

What I claim and desire to secure by Letters Patent is:
1. A method for treating a human host having viral regional ileitis infection comprising:
   a. repeatedly orally administering anti-viral regional ileitis infection effective amounts of a pharmaceutical composition which contains, as an active ingredient, 1-($\beta$hydroxyethyl)-2-methyl-5-nitromidazole to a human host in need of said treatment.
2. The method of claim 1 wherein:
   a. the dosage range of the composition in adult human hosts is about 31 mgs to 2,500 mgs per 24 hour period.
3. The method of claim 2 wherein:
   a. the dosage amount is substantially reduced following initial administration over a period including a plurality of months.
4. The method of claim 1 wherein:
   a. said composition is administered at a dosage of about 250 mgs per 24 hour period.

* * * * *